United States Patent [19]

Pigneul

[11] Patent Number: 5,092,860
[45] Date of Patent: Mar. 3, 1992

[54] SANITARY NAPKIN

[75] Inventor: Raymond Pigneul, Durrenentzen, France

[73] Assignee: Kaysersberg, SA, Kaysersberg, France

[21] Appl. No.: 624,516

[22] Filed: Dec. 7, 1990

Related U.S. Application Data

[63] Continuation of Ser. No. 410,519, Sep. 21, 1989, abandoned.

[30] Foreign Application Priority Data

Sep. 21, 1988 [FR] France ............... 8812343

[51] Int. Cl.[5] .............................. A61F 13/15
[52] U.S. Cl. .................. 604/380; 604/385.1
[58] Field of Search ............ 604/358, 385.1, 386, 604/387, 389, 391, 393, 394–397, 379–380, 381–383

[56] References Cited

U.S. PATENT DOCUMENTS

| | | |
|---|---|---|
| 2,747,575 | 5/1956 | Mercer ............... 604/385.1 |
| 3,442,268 | 5/1969 | Bird ............... 604/380 |
| 3,575,174 | 4/1971 | Mogor ............... 604/385.1 |
| 3,593,717 | 7/1971 | Jones, Sr. ............... 604/378 |
| 3,695,269 | 10/1972 | Malaney ............... 604/366 |
| 3,759,262 | 9/1973 | Jones, Sr. ............... 604/378 |
| 3,814,101 | 6/1974 | Kozak ............... 604/366 |
| 3,881,490 | 5/1975 | Whitehead et al. ............... 604/380 |
| 4,184,498 | 1/1980 | Franco ............... 604/375 |
| 4,397,644 | 8/1983 | Matthews et al. ............... 604/378 |
| 4,623,340 | 11/1986 | Luceri ............... 604/378 |
| 4,701,177 | 10/1987 | Ellis et al. ............... 604/358 |
| 4,710,186 | 12/1987 | DeRossett et al. ............... 604/383 |
| 4,752,349 | 6/1988 | Gebel ............... 604/380 |
| 4,758,240 | 6/1988 | Glassman ............... 604/379 |
| 4,758,241 | 7/1988 | Papajohn ............... 604/387 |
| 4,781,710 | 11/1988 | Megison et al. ............... 604/385.1 |
| 4,790,838 | 12/1988 | Pigneul et al. ............... 604/385.1 |
| 4,828,555 | 5/1989 | Hermansson ............... 604/379 |

FOREIGN PATENT DOCUMENTS

| | | |
|---|---|---|
| 0137725 | 4/1985 | European Pat. Off. . |
| 0173068 | 3/1986 | European Pat. Off. . |
| 1489626 | 7/1967 | France ............... 604/378 |

Primary Examiner—John D. Yasko
Assistant Examiner—Sharon Finkel
Attorney, Agent, or Firm—Breiner & Breiner

[57] ABSTRACT

An elongated sanitary napkin having a longitudinal central area suitable for positioning in a user's crotch area is provided. The sanitary napkin has an upper body contacting side and a lower garment contacting side. The napkin includes an elongated absorbent core delimited by a pair of longitudinal edges and a pair of transverse edges. The absorbent core is covered on at least its upper surface with a body fluid pervious facing and on its bottom surface with a body fluid impervious facing. The sanitary napkin is characterized by the inclusion in its upper body contacting side of two series of discrete indentations. One series of indentations is positioned adjacent to one of the longitudinal edges of the absorbent core and the other series of indentations is positioned adjacent to the opposite longitudinal edge of the absorbent core.

11 Claims, 2 Drawing Sheets

U.S. Patent        Mar. 3, 1992        Sheet 1 of 2        5,092,860
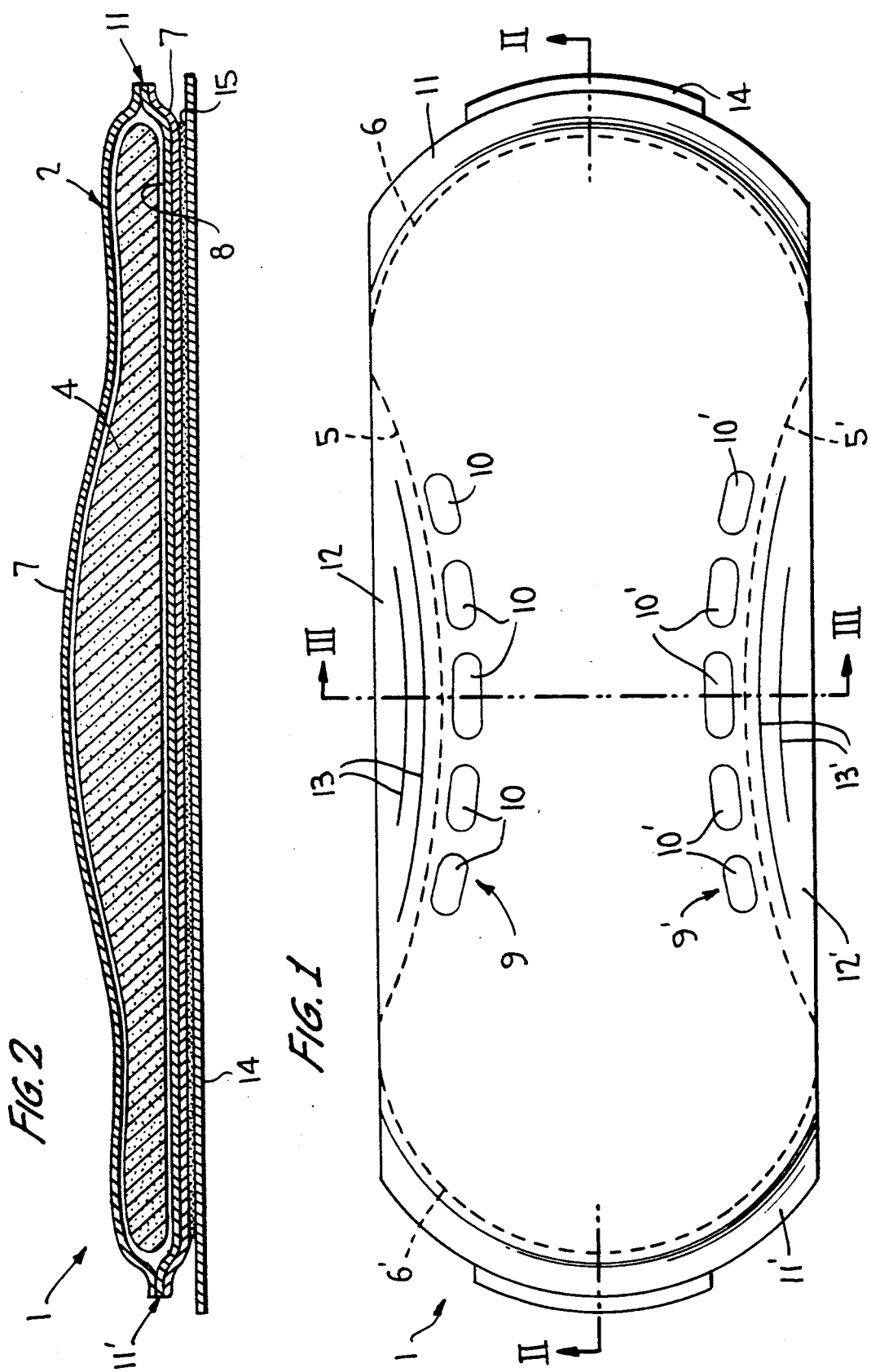

SANITARY NAPKIN

This is a continuation of copending application Ser. No. 07/410,519 filed Sept. 21, 1989 now abandoned.

FIELD OF INVENTION

The present invention is directed to a disposable sanitary napkin suitable for feminine hygiene use. More specifically, the invention involves a sanitary napkin having an elongated absorbent core covered by a facing which is pervious to body fluids and which has, in the central portion of its body contacting side, two series of discrete compressed areas which form indentations. One series is preferably substantially parallel and adjacent to one of the longitudinal edges of the absorbent core while the other series is preferably substantially parallel to the absorbent core s opposite longitudinal edge. This arrangement provides for good contact between the body contacting side of the napkin and the mucosa, better penetration of body fluids into the absorbent core and assures adequate maintenance of the sanitary napkin's shape, while providing flexibility for the user's comfort.

BACKGROUND OF THE INVENTION

Absorbent structures, such as sanitary napkins used for feminine hygiene purposes, having an elongated absorbent core covered on the body contacting side with a body fluid pervious facing which is potentially hydrophobic and covered on the garment contacting side by an impervious sheet is known in the art. The pervious facing can be either an apertured film or a non-woven material and the impervious sheet can, for example, be a polyethylene film. The absorbent core is generally made of cellulosic fibers, such as paper derived fibers called fluff which are obtained by dry stripping fibers from a paper pulp sheet. The absorbent core can also be made out of sphagnum or any other conventionally used absorbent material.

The above type of absorbent structures have been the subject of numerous research efforts aimed at obtaining a clean and dry contact surface through the appropriate choice of a fluid pervious facing material and through improving the facing's absorption properties by creating one or more channels in the upper surface of the absorbent core. The following references can be cited respectively in this regard: U.S. Pat. No. 3,695,269; U.S. Pat. No. 3,814,101; and EP-A-172,420; U.S. Pat. No. 4,184,498 and EP-A-137,725.

None of these absorbent structures, however, have provided complete satisfaction with regard to the two problems addressed by the studies.

EP-A-173,068 describes a sanitary napkin aimed at reducing both of the above-mentioned defects of sanitary napkins which are produced in a conventional manner, i.e., the staining and/or wetting of the upper facing and the poor distribution of fluids throughout the absorbent core. The sanitary napkin described in EP-A-173,068 includes an elongated absorbent core having an upper or body contacting surface and a bottom or garment contacting surface. The absorbent core is hollowed out in the body contacting surface by means of at least one elongated groove which forms a channel suitable for transporting body fluids, usually in a longitudinal direction. The sanitary napkin has, among other things, a hydrophobic facing which is pervious to body fluids and which covers the body contacting surface containing the hollow channel. For the body contacting surface to remain dry and clean when using a hydrophobic facing, the facing must extend down into the channel and be attached to the bottom of the channel (page 4, line 15-31). If the facing overlies the channel, contrary to the teaching of EP-A-173,068, the objectives sought will not be obtained and unfavorable results are observed from both the aesthetic and functional points of view (page 4, line 31 to page 5, line 2). The channel width and depth are stated to not be critical so long as the dimensions are adequate to insure its fluid transporting function (page 8, lines 22-25). The sanitary napkin described and shown in the example only utilizes a single channel which is located in the center of the body contacting surface. Such a sanitary napkin has turned out to be unsatisfactory because the channel hollowed out in the upper surface produces a rigidity to the structure which is prejudicial to the user's comfort.

BRIEF DESCRIPTION OF THE INVENTION

A primary purpose of the present invention is to provide a sanitary napkin whose upper or body contacting surface remains clean and dry during use and which has adequate shape retention characteristics while, at the same time, retaining sufficient flexibility to provide for user comfort. The sanitary napkin of the present invention, as claimed and described, provides these properties.

According to the present invention, a sanitary napkin is provided which is elongated in shape and has a central longitudinal portion which is suitable for positioning in a user's crotch area. The upper surface of the napkin is in contact with the user's body during use and the bottom surface of the napkin is in contact with the user's garment. The napkin has an elongated absorbent core delimited by longitudinal and transverse edges, with at least the upper surface or body facing side of the core being covered with a body fluid pervious facing or sheet and the bottom or garment facing surface being covered with a body fluid impervious facing or sheet. The sanitary napkin is characterized by the fact that its upper body contacting surface contains in its central area, two series of discrete compressed areas which form indentations or depressions. One series of indentations is positioned adjacent to one of the longitudinal edges of the absorbent core while the other series of indentations is positioned adjacent to the absorbent core's opposite longitudinal edge.

In one preferred embodiment of the invention, each series of indentations is positioned substantially parallel to the longitudinal edge of the absorbent core to which it is adjacent.

The two series of indentations can be made to extend over substantially the entire length of the central portion of the sanitary napkin which, when the napkin is being worn, is found in the crotch area of the user's garment, or can be made to extend beyond the central portion of the napkin into either end area.

According to a preferred embodiment of the present invention, the absorbent core has an anatomical shape wherein the central area is narrowed. In this embodiment, each of the longitudinal edges of the absorbent core has an incurved section which forms a bi-concave zone in the central area of the napkin.

The indentations present in the upper surface of the sanitary napkin, according to the invention, can have any shape. They can, for example, be substantially rectangular, circular, etc. The indentations of each of the two series can be either identical or different.

An important feature of the invention is that each of the series of indentations be discrete or discontinuous, i.e., each of the series includes a succession of separated compressed areas which form indentations. Accordingly, alternating raised areas and compressed areas are present in the central portion of the napkin along each longitudinal edge thereof.

The two discrete series of indentations, according to the invention, result in the provision of a swelling in the central portion of the sanitary napkin producing a pronounced convexity in the upper body contacting side of the napkin. This convexity insures good contact of the napkin with the mucosa and also serves to stretch the body fluid pervious facing, thereby improving fluid penetration into the absorbent core.

Further, the two discrete series of indentations, according to the invention, provides good shape retention characteristics to the sanitary napkin, while also allowing for sufficient flexibility in the napkin structure to provide for user comfort.

The indentations, according to the invention, can be formed using any suitable means, such as for example, the process described in French Patent No. 2,590,161 which makes use of a number of elements, each capable of forming the desired indentations.

BRIEF DESCRIPTION OF DRAWINGS

The invention is illustrated in reference to FIGS. 1, 2 and 3.

FIG. 1 is a plane view of the upper or body contacting side of an anatomically shaped sanitary napkin according to the present invention's preferred embodiment.

FIG. 2 is a cross-sectional view taken along line II—II of the sanitary napkin illustrated in FIG. 1.

DESCRIPTION OF THE PRESENTLY PREFERRED EMBODIMENT

Figure 3:
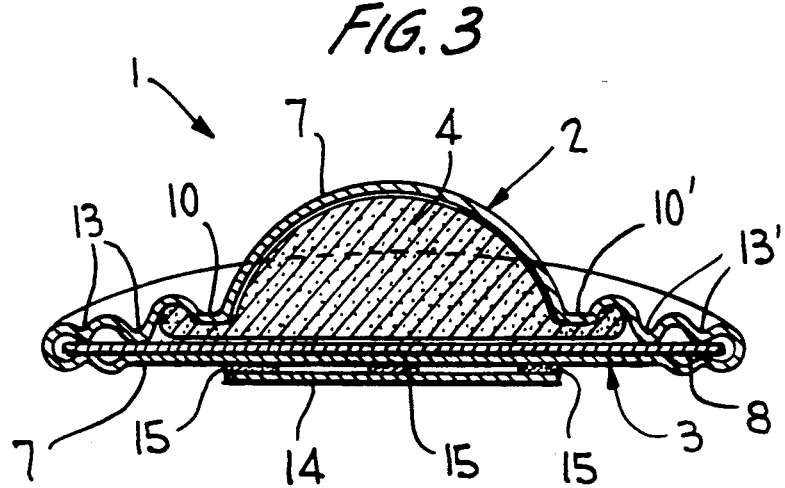
FIG. 3 is a cross-sectional view taken along line III—III of the sanitary napkin illustrated in FIG. 1.

FIGS. 1, 2, and 3 illustrate an elongated sanitary napkin 1 having an upper surface 2 for contacting the body or mucosa during use of the napkin and a lower surface 3 for contacting a user's garment. The sanitary napkin 1 contains an elongated absorbent core 4 delimited by a pair of longitudinal edges 5 and 5' and a pair of transverse edges 6 and 6'.

In the presently preferred embodiment, each of longitudinal edges 5 and 5' have an incurved portion which forms a bi-concave zone in the central portion of the sanitary napkin 1.

The upper or body facing side of the absorbent core 4 is covered with a body fluid pervious facing or sheet 7. The opposite side or bottom of the absorbent core is covered with an impervious facing or film 8. In the illustrated embodiment, facing 7 completely surrounds absorbent core 4 and thereby also covers impervious facing 8 as well. The pervious facing, however, can cover only the top portion of the absorbent core if desired. In either case, the transverse edges of the pervious and impervious facings are sealed together in sections 11 and 11'. Preferably, facing 7 is wider than the absorbent core in the bi-concave area of longitudinal edges 5 and 5' so as to form side flaps 12 and 12' which are adhered together, such as by glue, and include folds 13 and 13' therein.

A longitudinal protective strip or band 14 is attached to the sanitary napkin's 1 bottom surface 3 using adhesive elements 15. Protective strip 14 is removed just prior to use to expose adhesive elements 15. These adhesive elements serve to releasably attach sanitary napkin 1 to a user's garment to maintain the napkin in a desired location during use thereof.

The upper or body contacting side 2 of the sanitary napkin 1 has, in its central area, two series 9 and 9' of discontinuous or discrete indentations 10 and 10' which ar illustrated as being approximately rectangular in shape. One series 9 of indentations 10 is positioned adjacent to longitudinal edge 5 and the other series 9' of indentations 10' is positioned adjacent to longitudinal edge 5'.

As shown in FIG. 2, the structure of the sanitary napkin has a swelling in the central portion of absorbent core 4 producing a pronounced convexity in the body contacting side 3 of the central portion of the sanitary napkin 1. This convexity is formed due to the presence of the two series 9 and 9' of discrete indentations 10 and 10' in the sanitary napkin.

As will be apparent to one skilled in the art, various modifications can be made within the scope of the aforesaid description. Such modifications being within the ability of one skilled in the art form a part of the present invention and are embraced by the appended claims.

It is claimed:

1. An elongated sanitary napkin having an upper body contacting side and a bottom garment contacting side with a central longitudinal area for positioning in a user's crotch area comprising:
   (1) an elongated absorbent core delimited by a pair of longitudinal edges and a pair of transverse edges wherein said absorbent core is covered on at least its upper surface with a body fluid pervious facing and on its bottom surface with a body fluid impervious facing, and
   (2) two series of discrete indentations formed into said elongated absorbent core of said sanitary napkin in said upper body contacting side of said absorbent core wherein one series of said discrete indentation sis positioned adjacent to one of said longitudinal edges of said absorbent core, the other of said series of discrete indentation sis positioned adjacent to the opposite longitudinal edge of said absorbent core, neither of said two series of discrete indentations being formed in said transverse edges of said elongated absorbent core, and each of said series of discrete indentations being formed in said elongated absorbent core in a manner so as to provide a convexity in said upper body contacting side of said absorbent core.

2. The sanitary napkin according to claim 1 wherein each series of said discrete indentations is positioned substantially parallel to said longitudinal edge of said absorbent core to which said series is adjacent.

3. The sanitary napkin according to claim 1 wherein said discrete series of indentations covers substantially the entire length of the central area of said sanitary napkin.

4. The sanitary napkin according to claim 2 wherein said discrete series of indentations covers substantially the entire length of the central area of said sanitary napkin.

5. The sanitary napkin according to claim 1 wherein said series of discrete indentations extend beyond the central area of said napkin.

6. The sanitary napkin according to claim 2 wherein said series of discrete indentations extend beyond the central area of said napkin.

7. The sanitary napkin according to claims 1, 2, 3, 4, 5 or 6 wherein each of said longitudinal edges of said absorbent core has an incurved portion forming a biconcave are in said central area of said napkin.

8. The sanitary napkin according to claims 1, 2, 3, 4, 5 or 6 wherein said indentations are substantially rectangular in shape.

9. The sanitary napkin according to claim 7 wherein said indentations ar substantially rectangular in shape.

10. The sanitary napkin according to claims 1, 2, 3, 4, 5 or 6 wherein said indentations are substantially circular in shape.

11. The sanitary napkin according to claim 7 wherein said indentations are substantially circular in shape.

* * * * *